(12) United States Patent
Garner et al.

(10) Patent No.: US 8,396,538 B2
(45) Date of Patent: Mar. 12, 2013

(54) METHOD AND APPARATUS FOR IMPROVING SIGNAL TO NOISE RATIO OF ECG SIGNALS TO FACILITATE CARDIAC BEAT DETECTION

(75) Inventors: Garth Garner, Tigard, OR (US); Jie Lian, Beaverton, OR (US); Dirk Muessig, West Linn, OR (US)

(73) Assignee: Biotronik CRM Patent AG (DE)

( * ) Notice: Subject to any disclaimer, the term of this patent is extended or adjusted under 35 U.S.C. 154(b) by 74 days.

(21) Appl. No.: 12/954,418

(22) Filed: Nov. 24, 2010

(65) Prior Publication Data

US 2011/0130669 A1    Jun. 2, 2011

Related U.S. Application Data

(60) Provisional application No. 61/264,852, filed on Nov. 30, 2009.

(51) Int. Cl.
*A61B 5/04* (2006.01)

(52) U.S. Cl. ...................................................... 600/509

(58) Field of Classification Search .................... 600/509
See application file for complete search history.

(56) References Cited

U.S. PATENT DOCUMENTS

| | | | |
|---|---|---|---|
| 2009/0318821 A1 | 12/2009 | Demharter | |
| 2011/0306862 A1* | 12/2011 | Hayes-Gill et al. | 600/382 |
| 2012/0101430 A1* | 4/2012 | Robertson et al. | 604/66 |

OTHER PUBLICATIONS

Anonymous: 2006, "Electrocardiography I Laboratory", Cleveland Medical Devices, Inc., pp. 1-17, (Retrieved from the internet on Mar. 15, 2011: URL:http://biomed.engr.sc.edu/bme_lab/lab% 20reports/36%29%20ECG%20I.pdf) XP002628270.
Kligfield et al., 2007, "Recommendations for the standardization and interpretation of the electrocardiogram", *Heart Rhythm*, vol. 4, No. 3, pp. 394-412, XP005915945.
Wei et al., 1999, "A low-distortion filter method to reject muscle noise in multi-lead electrocardiogram systems", *Frontiers of Medical and Biological Engineering, VSP*. Zeist, NL, vol. 9, No. 4, pp. 315-330, XP009145991.
European Search Report, EP 10 19 2866, Mar. 21, 2011.

* cited by examiner

*Primary Examiner* — George Manuel
*Assistant Examiner* — Robert N Wieland
(74) *Attorney, Agent, or Firm* — Craig A. Fieschko, Esq.; DeWitt Ross & Stevens S.C.

(57) ABSTRACT

Improving the signal-to-noise ratio of electrocardiogram (ECG) measurements facilitates cardiac beat detection in a human or animal patient. ECG signals measured either on the surface of the skin or subcutaneously from pairs of leads may be combined to calculate a differential signal. The measured signal may also be averaged to produce a second estimate. A point-by-point product of the differential signal and the averaged signal is generated if the sample pair has the same polarity. The product signals feature enhanced signal components and reduced noise components, thus improving the signal-to-noise ratio of the to respective input channels. Product signals are then subjected to peak detection through a conventional auto-sensing approach. Preliminary event detection results from the conditional product signals may then be aggregated, and final sense markers for ECG beat detection may be generated by means of a voting algorithm.

20 Claims, 11 Drawing Sheets

METHOD AND APPARATUS FOR IMPROVING SIGNAL TO NOISE RATIO OF ECG SIGNALS TO FACILITATE CARDIAC BEAT DETECTION

RELATED APPLICATION

This patent application claims the benefit of U.S. Provisional Patent Application No. 61/264,852, filed on Nov. 30, 2009, which is hereby incorporated by reference in its entirety.

TECHNICAL FIELD

The present invention generally relates to medical devices that measure cardiac electrical signals, analyze the cardiac electrical signals, and detect the cardiac beat for each cardiac cycle. More particularly, the present invention relates to a method and apparatus for robust cardiac beat detection from surface ECG or subcutaneous ECG signals by improving the signal to noise ratio of the ECG signals.

BACKGROUND

A standard 12-lead electrocardiogram (ECG) is a representation of the heart's electrical activity recorded from electrodes on the body surface. Since its invention by Willem Einthoven in 1904, ECG has been a standard diagnosis tool for evaluating cardiac function. Normal ECG tracing is comprised of different waves that represent a sequence of depolarization and repolarization of the atria and ventricles. For example, a P wave represents atrial depolarization, a QRS complex represents ventricular depolarization, and a T wave represents ventricular repolarization. From these ECG waves, a plurality of intervals may be calculated that reflect cardiac conduction properties (e.g., P wave duration, PR interval, and QRS duration), repolarization properties (e.g., QT interval), intrinsic heart rate (e.g., PP or RR intervals), etc. Collectively, these ECG waves and durations contain important diagnostic information regarding a patient's underlying cardiac condition.

However, many patients experience intermittent spontaneous cardiac arrhythmias such as, for example, sinus bradycardia, non-sustained ventricular tachycardia, or paroxysmal atrial fibrillation, events which may not be recorded during their clinic visits. In order to capture these infrequent arrhythmia episodes, external ECG monitoring devices such as Holter monitors are often prescribed to continuously monitor the patient's ECG. However, Holter recording has two inherent drawbacks. First, the memory capacity is limited, and most commercially available Holter machines can only record 24-hr or 48-hr surface ECG measurements. Second, the use of skin electrodes is inconvenient and uncomfortable for the patient, and is a significant source of measurement noise due to loose contact, muscle movement, and environmental factors. Consequently, the diagnostic yield of a Holter ECG is very limited.

To overcome these shortcomings, subcutaneous ECG monitors have been introduced. By implanting a small device with sensing electrodes underneath the skin, the subcutaneous ECG monitor can record a subcutaneous ECG that resembles the surface ECG. The subcutaneous ECG monitor can be configured as a loop recorder, so that it continuously records newly acquired subcutaneous ECG signals while discarding the old recordings. When experiencing symptoms, a patient can use a handheld device that communicates with the subcutaneous device to trigger a snapshot of the recordings. Alternatively, the implantable device can be programmed to automatically trigger a snapshot of the subcutaneous ECG upon detection of an arrhythmic episode. The recorded snapshots can then be transmitted over the telephone or over a wireless network to a physician's office for clinical review. Because the loop recorder continuously refreshes its memory, it can be carried for long periods of time. Thus it is ideal for capturing ECG traces of infrequent episodes such as syncope. Recently, subcutaneous ECG recording has also become a useful means to monitor the cardiac rhythm after ablation of atrial fibrillation, to determine the ablation efficacy and to adjust therapeutic treatments.

Regardless of the specific ECG recording apparatus (e.g., ECG machines, bedside ECG monitors, Holter ECG monitors, subcutaneous ECG devices), reliable beat detection is the prerequisite for further ECG processing and clinical diagnosis. Despite decades of research, ECG beat detection has remained a technical challenge. On the one hand, many factors can cause over-sensing (false detection) of cardiac beats, such as large T waves, wide QRS complexes, muscle noise, electromagnetic interference (EMI), and the like. On the other hand, under-sensing (missed detection) of cardiac beats is also common for ECG signals that have a small signal to noise ratio. Existing methods for real-time ECG beat detection are either computationally complex, and therefore not suitable for implementation in an embedded system, or oversimplified so that they rely solely on ECG metrics such as peak amplitude, peak slope, etc., with or without an adaptive sensing threshold, and thus they result in unsatisfactory performance.

For at least the reasons given above, there is a need to provide a method and apparatus for more accurate and efficient detection of cardiac beats in response to surface ECG or subcutaneous ECG recordings.

SUMMARY

The present disclosure provides a novel method and apparatus for improving the signal to noise ratio of surface ECG or subcutaneous ECG for robust cardiac beat detection in a human or animal subject. According to a preferred embodiment, at least three electrodes are connected to a multiplex input that measures surface ECG or subcutaneous ECG signals in three sensing leads (AB, BC, CA) that form Einthoven's triangle, in the conventional manner. Signals measured from two such leads (BC, CA) may be combined to calculate a differential signal, as a first estimate of the signal measured in the third lead (AB). Preferably, AB is also processed through a moving average filter to produce a second estimate of the signal. A conditional product signal ($P_{AB}$) may then be obtained by generating a point-by-point product of the differential signal (the first estimate) and the averaged signal (the second estimate) if the sample pair has the same polarity, or by setting $P_{AB}$ to zero if the sample pair has different polarity. Similarly, conditional product signals ($P_{BC}$ and $P_{CA}$) may be obtained. Compared with the measured signals, the conditional product signals have enhanced signal components and reduced noise components, thus improving the signal to noise ratio of the respective input channels. The conditional product signals ($P_{AB}$, $P_{BC}$, $P_{CA}$) are then subjected to peak detection through a conventional auto-sensing approach that involves both signal blanking and adaptive thresholding. Preliminary event detection results from all three conditional product signals may then be aggregated, and final sense markers for ECG beat detection may be generated by means of a voting algorithm.

The details of the invention can be understood from the following drawings and the corresponding text descriptions.

DETAILED DESCRIPTION

Figure 1:
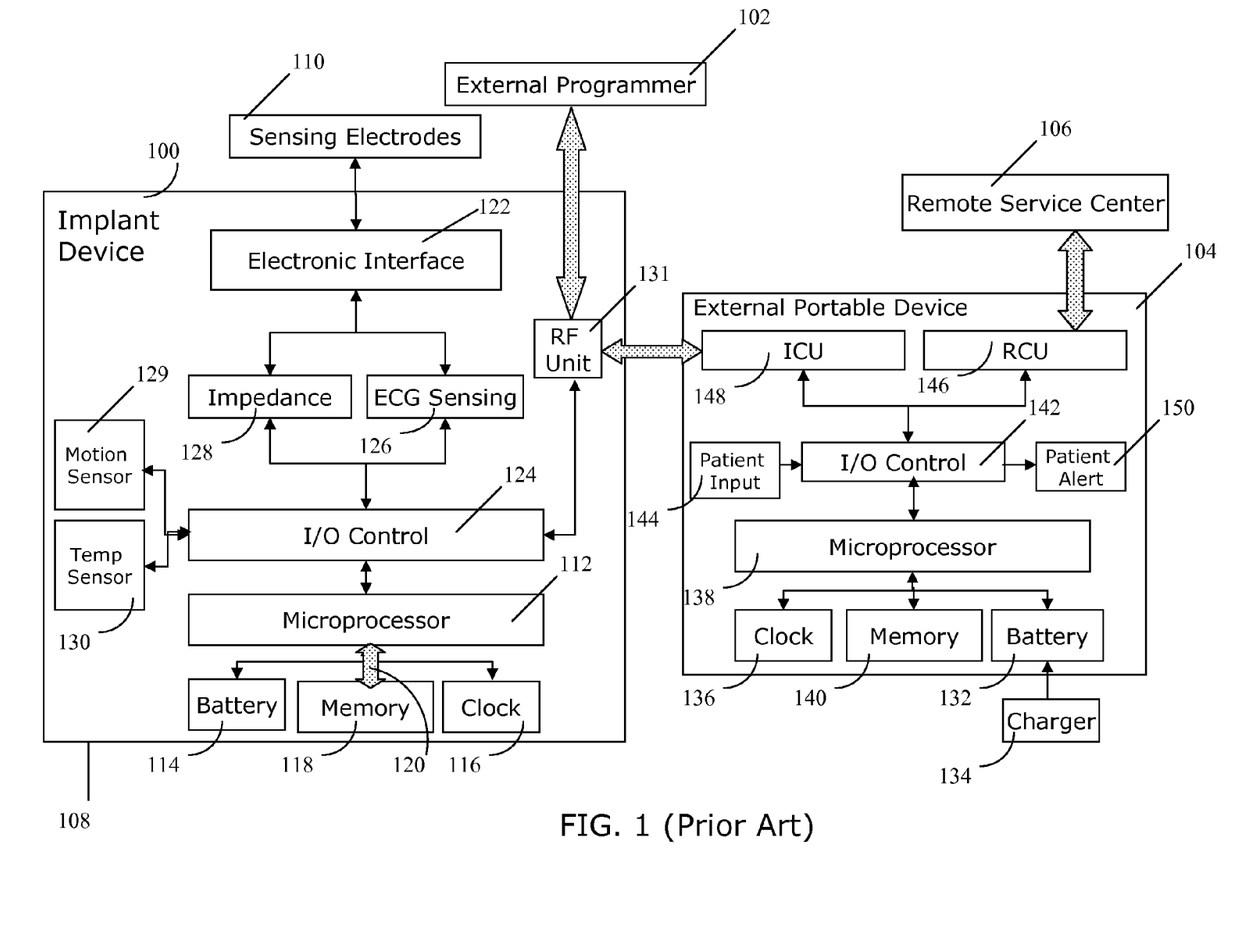
FIG. 1 shows a block diagram of a prior art system comprising an implantable subcutaneous ECG monitoring device, and its interfaces with an external programming device and an external portable device, which further communicates with a remote service center.

FIG. 1 shows a block diagram of an implantable device 100 for subcutaneous ECG monitoring, and its interfaces with an external programmer 102 and an external portable device 104, which further communicates with a remote service center 106.

With reference to FIG. 1, the implantable device 100 consists of electronic circuitry hermetically sealed inside a can 108, preferably made from a biocompatible conductive material such as titanium; an optional non-conductive header (not shown) attached to the can 108; and three or more sensing electrodes 110, with or without leads (not shown) connected to the header. The sensing electrodes 110, which are electrically isolated from one another, are preferably mounted on an outer surface of the can 108, or outside the header (if available), or at a distal end of the leads (if available). For subcutaneous ECG recording, one or more pairs of sensing electrodes form a set of sensing vectors, wherein each pair of sensing electrodes is separated by an inter-electrode distance preferably greater than 3 cm.

Leads are optional for subcutaneous ECG recording. Generally, if the measured subcutaneous ECG amplitude is too small for reliable sensing, despite configuring different sensing vectors and recording at different anatomical locations, then one or more subcutaneous leads (equipped with distal electrodes attached) may be tunneled under the patient's skin and connected to the header, so that larger subcutaneous ECG amplitudes may be measured by increasing the inter-electrode distance between the lead electrode and the can or between the lead electrode and the header electrode.

Enclosed inside the hermetically sealed can 108, a microprocessor 112 and associated circuitry make up a controller of the implant device 100. Implant device 100 is powered by a battery 114, and maintains an internal system clock 116 for timing operations. The microprocessor 112 communicates with a memory 118 via a bi-directional data bus 120. The memory 118 preferably comprises a ROM or RAM for program storage and a RAM for data storage.

The sensing electrodes 110 are first connected to an electronic interface 122 that preferably is includes feedthrough circuitry for noise reduction, high voltage protection circuitry, switch network circuitry for sensing channel selection, and front-end analog filters, as is well known in the field. The configuration of the interface circuitry (e.g., filter settings, sensing channel selection, etc.) may be programmed by the microprocessor 112.

The microprocessor 112 connects to an I/O control unit 124 to manage the input and output of the implant device 100. One input signal is the subcutaneous ECG signal measured by the sensing electrodes 110. After pre-processing by circuitry within electronic interface 122, the subcutaneous ECG signal is further processed by the ECG sensing unit 126, which may include amplifiers, analog-to-digital converters, digital filters, etc., as is known in the art. Another input signal is an impedance (Z) signal 128 measured between the sensing electrodes 110. By injecting a small constant current (e.g., 100 uA, preferably biphasic) between two electrodes while measuring a voltage difference between the same or a different pair of electrodes, the impedance may be calculated, using Ohm's law, as the ratio of the measured voltage difference and the injecting current. As is known in the art, the impedance signal 128 provides useful information about the integrity of the sensing channel. In addition, an impedance signal sensed by an impedance measurement unit 128 may be further processed by the microprocessor 112 to extract other aspects of the physiological status of the patient, such as respiration rate.

Other types of biological signals measured by specific sensors may also serve as input to the implant device 100. For example, an on-board accelerometer can serve as a motion sensor 129 that provides a patient's activity signal to the implant device 100, and a temperature sensor 130, either located on-board or embedded in a lead, may provide a subcutaneous temperature signal to the implant device 100. Other types of input signals include, but are not limited to, a subcutaneous pressure signal measured by a pressure sensor, an acoustic signal measured by an acoustic sensor, a subcutaneous pH signal measured by a pH sensor, and the like.

By running a program stored in the memory 118, microprocessor 112 also sends instructions to the ECG sensing unit 126, the impedance measurement unit 128, and other input is measurement units to control acquisition of these signals by adjusting parameters such as gain, offsets, filter settings, sampling frequency, sampling resolution, and the like.

Biological signals thus acquired are then stored in the device memory 118 and analyzed by programming the microprocessor 112. For example, the microprocessor 112 analyzes acquired subcutaneous ECG signals to detect a characteristic peak in the QRS complex. Such QRS peak detection can be achieved by many different means. One embodiment is to use an auto-sensing program that applies a detection hold-off period after each peak detection, and then automatically adjusts a sensing threshold, which is adaptive to the measured peak amplitude of the QRS complex, and which varies in accordance with a predetermined time dependence. One exemplary auto-sensing method is disclosed in U.S. Pat. No. 5,891,048, assigned to the present assignee. In the present disclosure, however, a more robust ECG beat detection method is described in detail below.

Accordingly, the implant device 100 measures intervals between pairs of adjacent peaks in the detected QRS complexes. These measured intervals, termed RR intervals, may be stored in the device memory 118 according to predefined storage modes. One typical mode is the queue-loop mode, meaning that the measured RR intervals are stored in a predefined memory space, and while the allocated memory space is full, the newly measured RR intervals replace the oldest stored RR interval data. Another typical mode is a snapshot mode, meaning the measured RR intervals are stored in a predefined memory space, and while the allocated memory space is full, the newly measured RR intervals are not stored until the microprocessor 112 decides to store another episode of RR intervals. Yet another typical mode is a mixed mode, in which one or more segments of allocated memory space store the RR intervals in queue-loop mode, whereas one or more segments of separately allocated memory space store the RR intervals in snapshot mode.

Similarly, the microprocessor 112 may also continuously analyze the acquired subcutaneous ECG signals to measure other metrics of the QRS complex, such as the width of the QRS complex; the positive or negative peak amplitude of the QRS complex, the absolute area under the QRS complex, the maximum positive or negative slopes of the QRS complex, the dominant frequency component of the QRS complex, the complexity measures (e.g., sampled entropy) of the QRS complex, and so on. Likewise, the time series of these measured metrics are stored in the device memory for further analysis.

The implant device 100 also includes a radio-frequency (RF) telemetry unit 131. The RF telemetry unit may be of a type well known in the art for conveying various information obtained from the implant device 100 to the external programmer 102, or for receiving programming parameters from the external programmer 102 and then conveying the parameters to the implant device 100. In one embodiment, the external programmer 102 interrogates the implant device 100 to obtain the status (e.g., battery status, sensing channel impedance) of implant device 100 or to obtain data recorded by the implant device 100, such as, for example, peak amplitude of the QRS complexes, statistics of measured RR intervals). In another embodiment, the external programmer 102 may be used to activate or deactivate selected programs or to update programmable parameters of the implant device 100.

In addition, the external portable device 104 to be described hereinafter, may also communicate bi-directionally with the implant device 100 through the implant communication unit (ICU) 148. Preferably, the data that may be received from or sent to the external portable device 104 are more limited as compared to the data that may be received from or sent to the external programmer 102.

In a preferred embodiment, data transmitted from the external portable device 104 to the implant device 100 may be in the form of simple commands, such as "trigger a snapshot of the acquired subcutaneous ECG," or "retrieve most recently diagnostic information from the implanted device 100." These commands set the implant device 100 into one of a number of modalities wherein each modality is determined and controlled by parameters that can only be selected by a physician operating the external programmer 102 using a secure password or codes.

Data transmitted from the implant device 100 to the external portable device 104 preferably include a simple acknowledgment to confirm receiving the commands from the external portable device 104, and signals warning the detection of abnormal conditions, such as atrial fibrillation (AF), high ventricular rate (HVR), low ventricular rate (LVR), abnormal sensing impedance, abnormal temperature, and so on. Other diagnostic information, such as the AF burden, the frequency of ectopic beats, snapshots of RR intervals or subcutaneous ECG, and the like, may also be transmitted to the external portable device 104. Preferably, a physician operating the external programmer 102 using a secure password or codes controls the enable or disable condition as well as the amount of data that can be transmitted from the implant device 100 to the external portable device 104.

The external portable device 104 shown in FIG. 1 includes a power source, such as a lithium battery 132, which provides power to the electrical components of the device. The battery 132 is chargeable by connecting to an external charger 134. The external portable device 104 also maintains an internal clock 136 for timing its operations. The overall functioning of the external portable device 104 is controlled by its microprocessor 138, which reads and performs instructions stored in its associated memory 140. The instructions stored in memory preferably include instructions defining a communication protocol compatible with the implant device 100, and instructions defining a communication protocol compatible with the remote service center 106.

The microprocessor 138 communicates with an I/O control unit 142 to read patient input commands from a patient input device 144 such as a keypad or press switches. In an exemplary embodiment, one subset of the input commands is designed to configure the external portable device 104, for example, to turn on or off certain outputs as described hereinafter, or to select specific communication protocols. Another subset of the input commands is designed to establish communication between the external portable device 104 and the remote service center 106 through a remote communication unit (RCU) 146. For example, patient input device 144 may command the external portable device 104 to transmit diagnostic information (retrieved from the implant device 100) to the remote service center 106, and wait to receive acknowledgement. The third subset of the input commands is designed to establish communication between the external portable device 104 and the implant device 100 through an implant communication unit (ICU) 148. For example, patient input device 144 may command the external portable device 104 to transmit corresponding signals to the implant device 100 to trigger recording a snapshot of the subcutaneous ECG, to retrieve diagnostic information from the implanted device 100, etc. The ICU 148 also receives acknowledgements and related diagnostic information sent from the implant device 100, and conveys these data to the microprocessor 138 for storage in the memory 140.

According to one exemplary embodiment, upon receiving a predefined warning signal from the implant device 100 (e.g., detection of AF, HVR, LVR, abnormal sensing impedance, abnormal temperature, etc.), the microprocessor 138 communicates with the I/O control unit 142 to generate output in the form of a patient alert 150. Such an alert may be in the form of a visible message, for example, by illuminating a continuous or blinking light emitting diode (LED); a text message displayed in a liquid crystal display (LCD); an audible message such as a beep, ringing tone, or pre-recorded voice message played through a speaker; or in the form of discernible mechanical vibration produced by a vibrator. According to the patient's preference, different warning messages may be turned on or off. For example, at night, a visible warning message may be turned on while an audible warning message is turned off if the patient chooses not to be disturbed while sleeping even if the implant device detects a condition such as AF. In addition to generating warning messages, some diagnostic information (e.g., the heart rate) that is received from the implant device 100 and stored in memory 140 may also be provided to the patient in the form of visible or audible messages.

The external portable device 104, via its RCU 146, may further communicate with the remote service center 106. Such a long-range communication apparatus may be in the form of a mobile radio network, a fixed-line telecommunication network, or the Internet, as is well known in the art. Examples of such a long-range communication apparatus have been taught in U.S. Pat. No. 6,470,215, U.S. Pat. No. 6,574,509, and U.S. Pat. No. 6,622,043, all of which are assigned to the assignee of the present invention and all of which are herein incorporated by reference in their entirety.

In one embodiment, the external portable device 104 transmits status information pertaining to implant device 100 (e.g., battery status, sensing impedance) as well as relevant diagnostic information (e.g., AF burden, ectopic beat frequency) to the remote service center 106 according to a predefined transmission frequency and schedule (e.g., every night at midnight). In yet another embodiment, the external portable device 104 communicates with the remote service center 106 in a trigger mode, for example, upon receiving a warning signal from the implant device 100, or upon receiving a patient trigger. In such cases, the external portable device 104 transmits diagnostic information stored in device memory 140 (e.g., AF burden, mean heart rate, subcutaneous ECG snapshot) to the remote service center.

The remote service center 106 receives the information via compatible communication protocols, and then returns an acknowledgement to the external portable device 104, which may generate visible or audible output messages indicating receipt of the acknowledgement. Data received by the remote service center 106 is stored in a central database, and may be promptly presented to the patient's physician or to a responsible expert via fax, e-mail, or text messaging, as is customary in the art, or via a similar means of communication. By reviewing the received diagnostic information, the physician can evaluate the patient's condition and provide expert advice to a patient who wishes to consult the physician before taking any action in response to the warning signals generated by the external portable device 104.

A novel method and apparatus for cardiac beat detection from subcutaneous ECG recordings that may be obtained using the implant device 100 shown in FIG. 1 is disclosed hereinafter. It shall be understood that the same principles are also applicable to cardiac beat detection from surface ECG recordings obtained using conventional ECG machines, bedside ECG monitors, Holter ECG devices, automatic external defibrillators, and the like.

Figure 2:
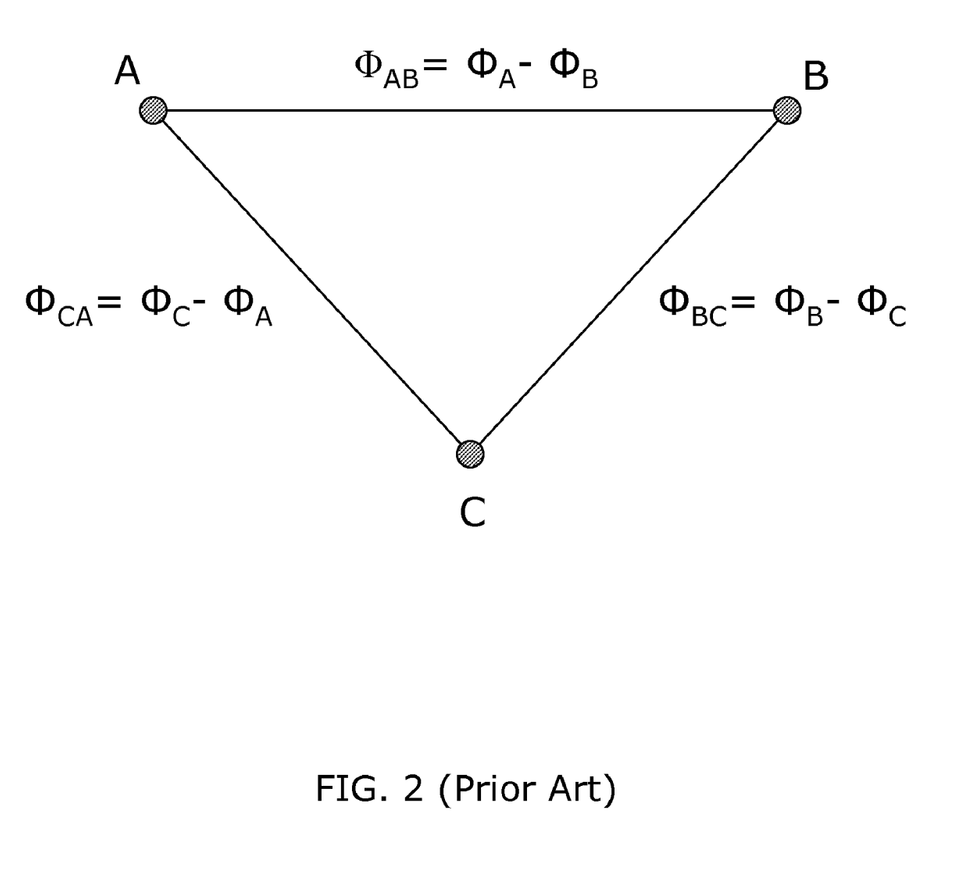
FIG. 2 shows a schematic drawing of three spatially distributed electrodes for use is with the implant device of FIG. 1 in measuring ECG or subcutaneous signals from three sensing vectors.

According to a preferred embodiment, at least three sensing electrodes 110 are preferably connected to the input channels of the implantable device 100 to measure the subcutaneous ECG. The three sensing electrodes 110 are implanted subcutaneously in a patient's chest so that the electrodes are spatially separated, preferably by an inter-electrode distance exceeding 3 cm for each pair. As illustrated in FIG. 2, three sensing electrodes (labeled A, B, and C) arranged in a triangle, as is commonly done, measure three focal subcutaneous electric potentials $\Phi_A$, $\Phi_B$, and $\Phi_C$, respectively. Pairs of sensing electrodes form three sensing vectors, or leads. Specifically, electrodes A and B form lead AB that measures $\Phi_{AB}$, which is the voltage difference between $\Phi_A$ and $\Phi_B$. Similarly, electrodes B and C form lead BC that measures $\Phi_C$, which is the voltage difference between $\Phi_B$ and $\Phi_C$. Likewise, electrodes C and A form lead CA that measures $\Phi_{CA}$, which is the voltage difference between $\Phi_C$ and $\Phi_A$. Hence, the triangular configuration for voltage measurement shown in FIG. 2 provides at least three subcutaneous ECG signal input channels for the subcutaneous implantable device 100.

Figure 3:
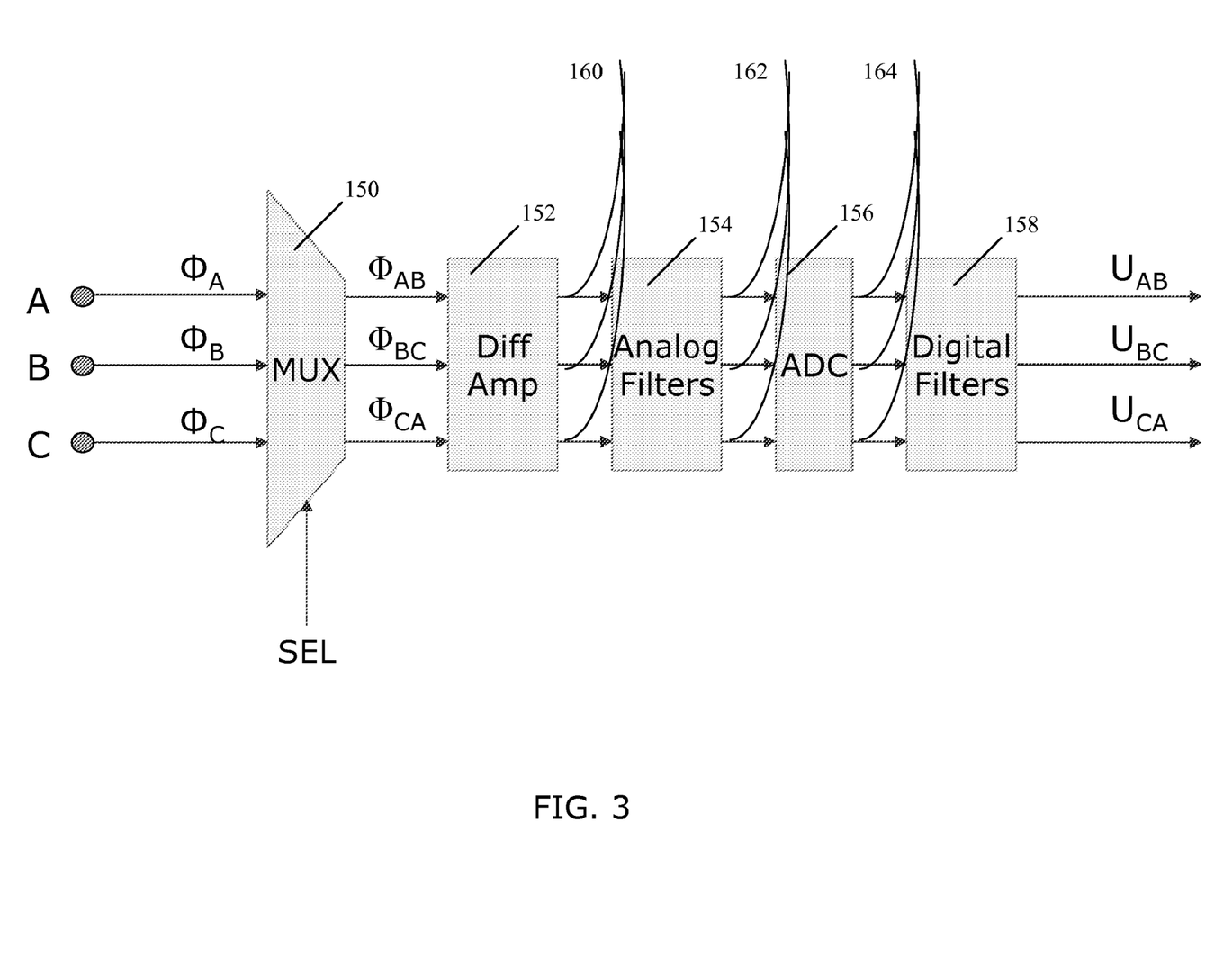
FIG. 3 shows a simplified block diagram of the front-end of the implantable device shown in FIG. 1, that includes a multiplexer and a plurality of signal pre-processing units.

FIG. 3 shows a simplified block diagram of the front-end of a preferred embodiment of the implantable device 100 that receives analog voltage signals from the three sensing electrodes and generates three channels of multiplexed digital output. In FIG. 3, the front-end circuit as part of the electronic interface 122 preferably includes five signal processing layers: a multiplexer 150, differential amplifiers 152, analog filters 154, an analog-to-digital converter (ADC) 156, and digital filters 158.

As shown in FIG. 3, three subcutaneous sensing electrodes (A, B, C) measure the focal subcutaneous electric potentials $\Phi_A$, $\Phi_B$, and $\Phi_C$, respectively, and are connected to the input of multiplexer 150. The multiplexer 150 is controlled by microprocessor 112, which divides the time domain into three recurrent timeslots of fixed length, and then sequentially selects two sensing electrodes 110 at a time to obtain three time-multiplexed differential voltage signals $\Phi_{AB}$, $\Phi_{BC}$, $\Phi_{CA}$. In synchronization with the system clock 116, the microprocessor 112 selects the pair of sensing electrodes 110 according to a designated sampling frequency which determines the multiplexing timeslot length. For example, if the sampling frequency is 256 Hz, then the multiplexing timeslot length is about 3.9 ms.

The multiplexed differential voltage signals ($\Phi_{AB}$, $\Phi_{BC}$, $\Phi_{CA}$) are connected to the differential amplifiers 152 which amplify the differential voltage signals while providing common mode rejection. Amplified differential voltage signals 160 are then connected to the analog filters 154, which include at least anti-aliasing low pass filters whose cut-off frequency corresponds to the highest frequency component of interest in subcutaneous ECG signals, e.g., 128 Hz. In addition, the analog filters 154 also include high pass filters with sufficiently low corner frequency, e.g., 0.5 Hz, to remove the DC offset component from each amplified differential voltage signal 160. Preferably, the analog filters 154 also include 50 Hz or 60 Hz notch filters to remove power-line interference.

Amplified and analog-filtered differential voltage signals 162 are then converted by the ADC 156 to digital signals 164 according to a predefined or user-programmable sampling frequency, e.g., 128 Hz, 256 Hz, 512 Hz, etc. The converted digital signals 164 are then further processed through digital filters 158 whose filter characteristics (e.g., filter type, order, gain, corner frequencies) are user-programmable. By adjusting the digital filter characteristics, a user may optimize signal quality for specific applications. For example, for reliable beat detection, a T wave may be attenuated to avoid T wave over-sensing.

Thus, the front-end of the implantable device 100 converts the analog voltage input from three sensing electrodes ($\Phi_A$, $\Phi_B$ and $\Phi_C$) to three channels of time-multiplexed digital subcutaneous ECG signals $U_{AB}$, $U_{BC}$ and $U_{CA}$. In a preferred embodiment, the gains and filter settings for all three channels in the front-end are the same.

Figure 4:
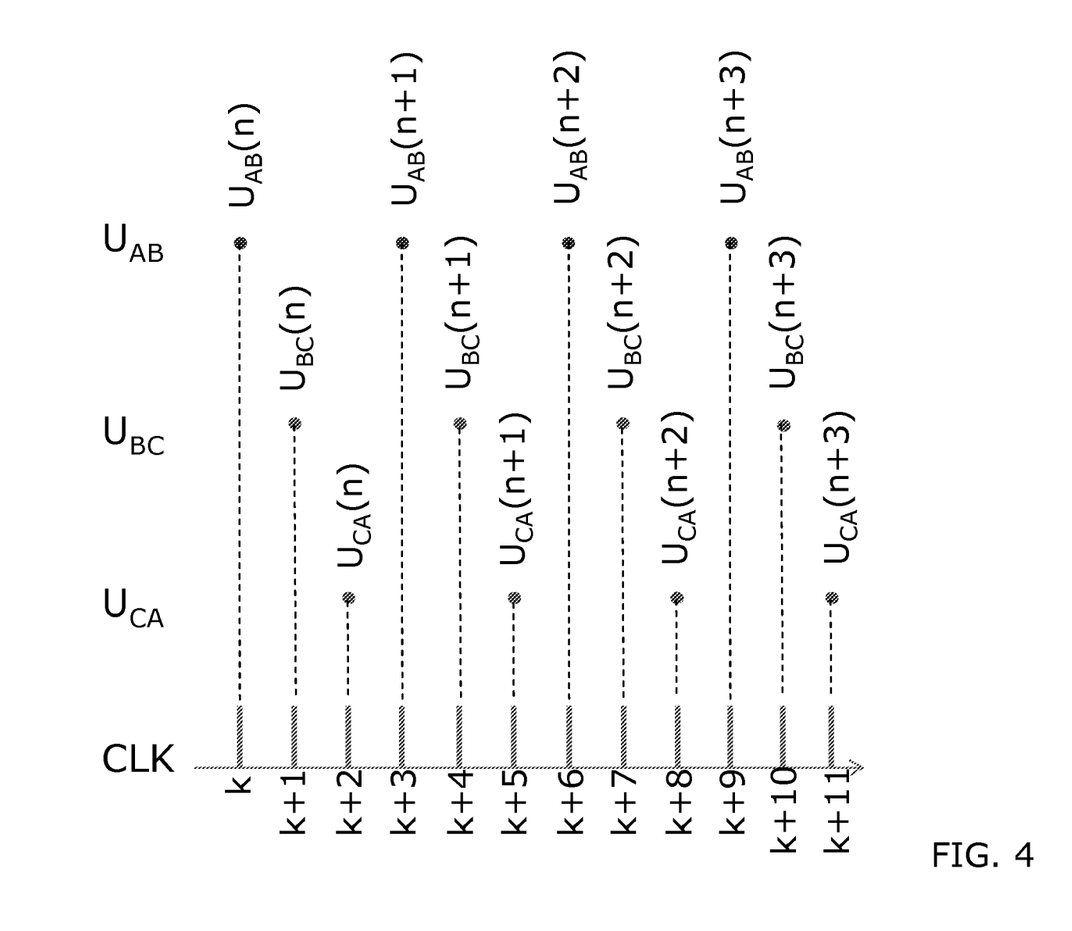
FIG. 4 shows a schematic drawing that illustrates how three subcutaneous signals may be multiplexed in synchronization with a sampling clock.

FIG. 4 shows a schematic drawing illustrating a way of multiplexing three-channel subcutaneous signals in synchronization with a sampling clock. At the time slot k, the multiplexer 150 controls the generation of one sample digital output $U_{AB}(n)$ representing the differential voltage in lead AB measured at the time slot k, where n is the sample index. At the next time slot k+1, multiplexer 150 controls the generation of one sample digital output $U_{BC}(n)$ representing the differential voltage in lead BC measured at the time slot k+1, wherein the sample index n remains unchanged. Then at the next time slot k+2, multiplexer 150 controls the generation of one sample digital output $U_{CA}(n)$ representing the differential voltage in lead CA measured at the time slot k+2, wherein the sample index n is still unchanged. Then at the next time slot k+3, multiplexer 150 controls the generation of one sample digital output $U_{AB}(n+1)$ representing the differential voltage in lead AB measured at the time slot k+4, wherein the sample index is increased to n+1. Following the similar steps, multiplexer 150 sequentially controls the generation of the sample output $U_{BC}(n+1)$, $U_{CA}(n+1)$, $U_{AB}(n+2)$, $U_{BC}(n+2)$, $U_{CA}(n+2)$, $U_{AB}(n+3)$, $U_{BC}(n+3)$, $U_{CA}(n+3)$ in the following time slots, and the process repeats. As a result, for each specific sample index, there is one digital sample in each of the three output channels. However, these three digital samples represent the differential voltages in respective leads that are measured at three different times.

Figure 5:
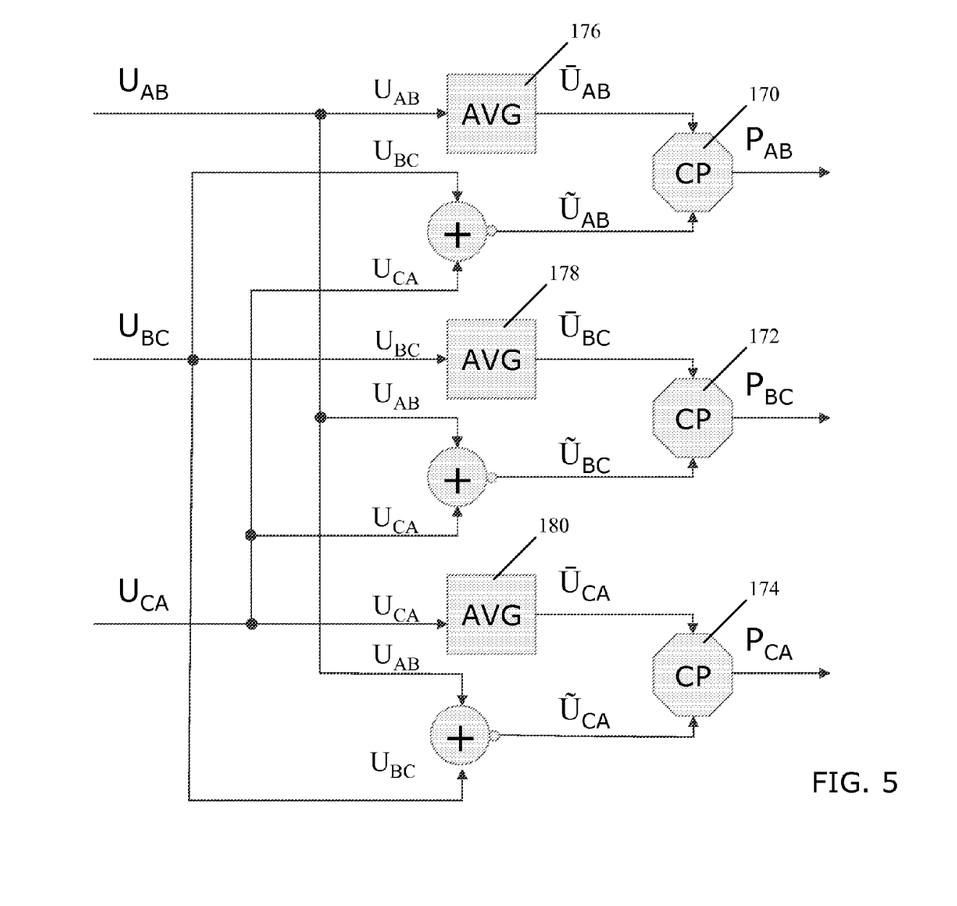
FIG. 5 shows a block diagram that illustrates a method for generating three conditional product signals from three multiplexed differential voltage signals.

FIG. 5 shows a block diagram illustrating a method of generating three conditional product signals ($P_{AB}$, $P_{BC}$, $P_{CA}$) from three multiplexed differential voltage signals ($U_{AB}$, $U_{BC}$, $U_{CA}$).

At an instant in time, cardiac electrical activity can be represented as a 3D dipolar vector, which may be projected onto the three sensing channels 110. Accordingly, $\Phi_C$ measures the far-field projection of the cardiac vector along the BC axis, $\Phi_{CA}$ measures the far-field projection of the cardiac vector along the CA axis, and $\Phi_{AB}$ measures the far-field projection of the cardiac vector along the AB axis. According to the principles of vector arithmetic, at a time t, $\Phi_{AB}(t)=-(\Phi_{BC}(t)+\Phi_{CA}(t))$, $\Phi_{BC}(t)=-(\Phi_{AB}(t)+\Phi_{CA}(t))$, and $\Phi_{CA}(t)=-(\Phi_{AB}(t)+\Phi_{BC}(t))$. Because the gains and filter settings for all three channels in the front-end are the same, the same arithmetic relationship would also hold true for the three digital signals had the data been sampled at the same time, that is, at any time instant t, $U_{AB}(t)=-(U_{BC}(t)+U_{CA}(t))$, $U_{BC}(t)=-(U_{AB}(t)+U_{CA}(t))$, and $U_{CA}(t)=-(U_{AB}(t)+U_{BC}(t))$.

However, because $U_{AB}$, $U_{BC}$, and $U_{CA}$ are time-multiplexed, for each specific sample index n, $U_{AB}(n)$, $U_{BC}(n)$, and $U_C(n)$ are sampled at three adjacent, rather than the same, time slots. Therefore, $-(U_{BC}(n)+U_{CA}(n))$ is only an approximate of $U_{AB}(n)$, $-(U_{AB}(n)+U_{CA}(n))$ is only an approximate of $U_{BC}(n)$, and $-(U_{AB}(n)+U_{BC}(n))$ is only an approximate of $U_{CA}(n)$.

With reference to FIG. 5, the differential voltage signals $U_{BC}$ and $U_{CA}$ are summed and then inverted to generate the signal $\tilde{U}_{AB}$, which is a first estimate of the signal $U_{AB}$. Similarly, $U_{AB}$ and $U_{CA}$ are summed and then inverted to generate the signal $\tilde{U}_{BC}$, which is a first estimate of the signal $U_{BC}$. Likewise, $U_{AB}$ and $U_{BC}$ are summed and then inverted to generate the signal $\tilde{U}_{CA}$, which provides a first estimate of the signal $U_{CA}$.

According to one embodiment, the signals $U_{AB}$ and $\tilde{U}_{AB}$ are processed through a conditional product (CP) unit 170 to generate a composite signal $P_{AB}$. Similarly, $U_{BC}$ and $\tilde{U}_{BC}$ are processed through a second CP unit 172 to generate the composite signal $P_{BC}$, and $U_{CA}$ and $\tilde{U}_{CA}$ are processed through a third CP unit 174 to generate the composite signal $P_{CA}$.

According to another embodiment, as described in FIG. 5, the signal $\tilde{U}_{AB}$ is further processed through a first moving average filter 176 to generate the signal $\overline{U}_{AB}$, which is a second estimate of the signal $U_{AB}$. Similarly, $U_{BC}$ is further processed through a second moving average filter 178 to generate the signal $\overline{U}_{BC}$, which is a second estimate of the signal $U_{BC}$, and $U_{CA}$ is further processed through a third moving average filter 180 to generate the signal $\overline{U}_{CA}$, which is a second estimate of the signal $U_{CA}$. The conditional product signal $P_{AB}$ may then be obtained from $\tilde{U}_{AB}$ and $\overline{U}_{AB}$, which are two different estimates of $U_{AB}$. Likewise, the conditional product signal $P_{BC}$ may be obtained from $\tilde{U}_{BC}$ and $\overline{U}_{BC}$, which are two different estimates of $U_{BC}$, and the conditional product signal $P_{CA}$ may be obtained from $\tilde{U}_{CA}$ and $\overline{U}_{CA}$, which are two different estimates of $U_{CA}$.

A benefit of using moving average filters is to better align the second estimated signals to the first estimated signals. With reference to FIG. 4, $U_{AC}(n)$ is sampled at the time slot k+1, and $U_C(n)$ is sampled at the time slot k+2. Their combination $-(U_{BC}(n)+U_{CA}(n))$ yields a first estimate of $U_{AB}$ had it been sampled between the time slots k+1 and k+2. Meanwhile, the average of $U_{AB}(n)$ and $U_{AB}(n+1)$ provides a second estimate of $U_{AB}$ had it been sampled between the same time slots k+1 and k+2. Similarly, $U_{AB}(n+1)$ is sampled at the time slot k+3, and $U_{BC}(n+1)$ is sampled at the time slot k+4. Their combination $-(U_{AB}(n+1)+U_{BC}(n+1))$ yields a first estimate of $U_{CA}$ had it been sampled between the time slots k+3 and k+4. Meanwhile, the average of $U_{CA}(n)$ and $U_{CA}(n+1)$ provides a second estimate of $U_{CA}$ had it been sampled between the same time slots k+3 and k+4. On the other hand, note that $U_{AB}(n+1)$ is sampled at the time slot k+3, and $U_{CA}(n+1)$ is sampled at the time slot k+5. Their combination $U_{AB}(n+1)+U_{CA}(n+1)$ yields a first estimate of $U_{BC}$ sample at the time slots k+4, which is exactly $U_{BC}(n+1)$. In this case, it is not necessary to apply a moving average to obtain a second estimate of $U_{BC}$ because $U_{BC}$ is already aligned with $U_{AB}+U_{CA}$. Alternatively, we can still apply a moving average filter to generate a second estimate of $U_{BC}$ without changing its alignment with $U_{AB}+U_{CA}$. For example, $U_{BC}(n+1)$ can be estimated as the average of its two neighboring samples, i.e., $(U_{BC}(n)+U_{BC}(n+2))/2$, or as a generalized weighted average, such as the average of three adjacent samples, i.e., $(U_{BC}(n)+2U_{BC}(n+1)+U_{BC}(n+2))/4$, wherein certain weighting factors in the generalized is weighted average may be set to zero, allowing for a case in which the second estimate reduces to the original signal itself.

Figure 6:
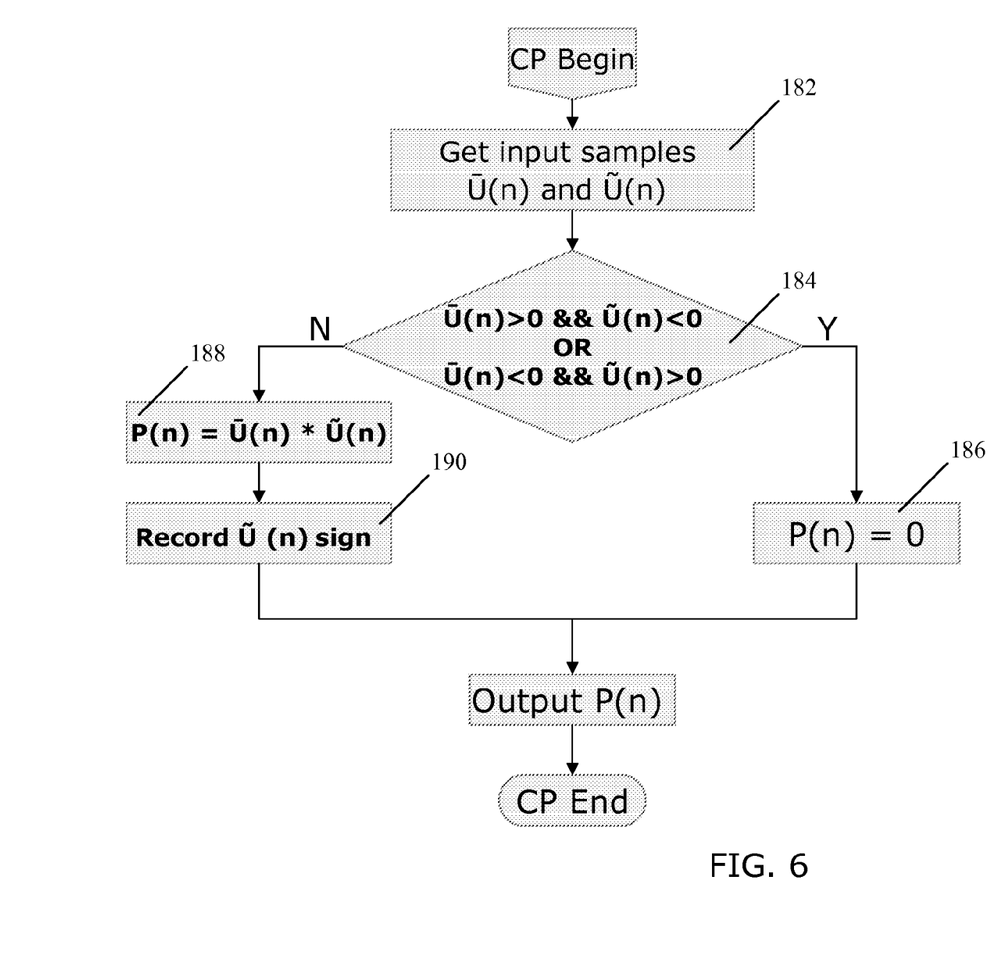
FIG. 6 shows a flowchart of a method for obtaining a conditional product signal.

Referring to FIG. 6, a flowchart is presented that describes implementation of the conditional product function performed by CP units 170, 172, and 174. Each CP unit processes two input signals, $\tilde{U}$ and $\overline{U}$, to generate the output signal P. For each sample index n, the CP unit receives, in a signal input step 182, a pair of input samples $\tilde{U}(n)$ and $\overline{U}(n)$. If, in a decision step 184, the sample pair have opposite signs, i.e., if $\tilde{U}(n)>0$ and $\overline{U}(n)<0$, or $\tilde{U}(n)<0$ and $\overline{U}(n)>0$, then product variable P(n) is set to 0 in step 186. Otherwise, P(n) is set to the product of the input samples, i.e., $P(n)=\tilde{U}(n)*\overline{U}(n)$ in step 188. In addition, the sign of $\overline{U}(n)$ or $\tilde{U}(n)$ is recorded in step 190 for later phase correction as described herein below. P(n) is the CP function output corresponding to the sample index n. Although not shown in FIG. 6, an alternative method entails setting P(n)=0 if $\tilde{U}(n)$ and $\overline{U}(n)$ have opposite signs, and $P(n)=\tilde{U}(n)+\overline{U}(n)$ or $P(n)=[\tilde{U}(n)+\overline{U}(n)]/2$ if $\tilde{U}(n)$ and $\overline{U}(n)$ have the same sign.

A normal subcutaneous ECG signal generally has distinctive signal components such as a P wave, a QRS complex, and a T wave. If a sufficiently high sampling rate is used, each of these signal components can be represented by multiple samples in the digitized signal. For example, a QRS complex with 100 ms duration can be represented by 25-26 samples using a sampling frequency of 256 Hz. Consequently, the morphology of the signal component is rarely affected by the input multiplexing. For example, the QRS complex morphology in channel $U_{AB}$ is almost the same no matter the signal is sampled at the time slots k, k+3, k+6, k+9, etc, or sampled at the time slots k+1, k+4, k+7, k+10, etc, or sampled at the time slots k+2, k+5, k+8, k+11, etc.

In contrast, many noises such as myopotentials, electromagnetic interference (EMI), and other such electrical activities originating outside the heart, have much higher frequency components. These noise components may be added to the subcutaneous ECG and shown as random impulses with relatively short durations. As a result, these noise components are more sensitive to input multiplexing. For example, assume the sampling frequency is 256 Hz. If a noise impulse has less than 4 ms duration, then it is very likely that the noise impulse is sampled at one channel at a certain time slot, but not sampled at two other channels due to multiplexing. Similarly, at the sampling frequency 256 Hz, a noise impulse with less than 8 ms duration may be sampled by two channels at two adjacent time slots, but not detected in the third channel. Even if the noise duration is longer and the noise component is sampled in all three channels, the noise component sampled in one channel may have very different morphology than the one estimated from the other two channels, because the noise amplitude may vary significantly from one time slot to the next time slot.

With reference to FIG. 6, because the signal component is not sensitive to multiplexing whereas the noise component is more sensitive to multiplexing, the CP unit can augment the signal component while suppressing the noise component. For example, assume the subcutaneous ECG in channel U shows a QRS complex at the sample index n. Then the signal component (sample amplitude of QRS waveform) is likely present in both its first estimate $\tilde{U}(n)$ and its second estimate $\overline{U}(n)$, and these two estimates likely have similar sample amplitude with the same sign. Thus, their product $P(n) = \tilde{U}(n) * \overline{U}(n)$ is positive, and augments more for larger sample amplitude (e.g., QRS peak). In contrast, assume the subcutaneous ECG in channel U is contaminated by noise at the sample index n. Then it is very likely that the noise component is not consistently present in both $\tilde{U}(n)$ and $\overline{U}(n)$. For example, noise component may be absent in $\tilde{U}(n)$ and/or $\overline{U}(n)$, or has reduced amplitude in $\tilde{U}(n)$ and/or $\overline{U}(n)$. Even if noise component is present in both $\tilde{U}(n)$ and $\overline{U}(n)$, it is likely that $\tilde{U}(n)$ and $\overline{U}(n)$ have very different amplitude and possibly have different signs. If $\tilde{U}(n)$ and $\overline{U}(n)$ have different signs, then their conditional product $P(n)$ is set to zero. If $\tilde{U}(n)$ and $\overline{U}(n)$ have very different amplitudes, then $P(n)$ may also be attenuated, e.g., when either $\tilde{U}(n)$ or $\overline{U}(n)$ is close to zero.

Figure 7:
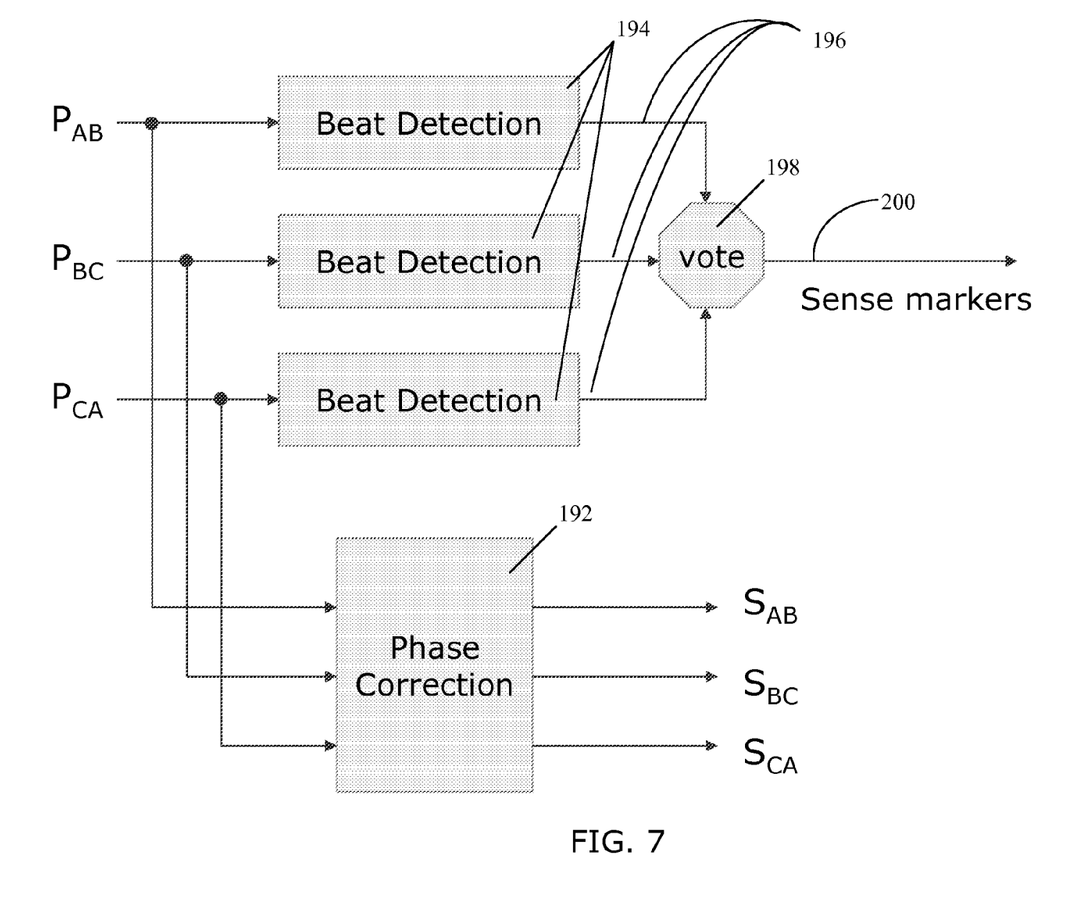
FIG. 7 shows a block diagram of a method for generating three phase-corrected conditional product signals and final sense markers by analyzing three conditional product input signals.

FIG. 7 shows a block diagram that shows how three channels of phase-corrected conditional product signals ($S_{AB}$, $S_{BC}$, and $S_{CA}$) and final sense markers are generated, by analyzing three input conditional product signals. Because the conditional product signals $P_{AB}$, $P_{BC}$, and $P_{CA}$ are always positive, it is desirable to restore the phase information (positive and negative deflections) embedded in the original signals $U_{AB}$, $U_{BC}$, and $U_{CA}$, for example, to facilitate morphological analysis of the subcutaneous ECG. This is achieved by feeding the conditional product signals $P_{AB}$, $P_{BC}$, and $P_{CA}$ to a phase correction unit 192, which generates respective phase-corrected signals $S_{AB}$, $S_{BC}$, and $S_{CA}$. According to a preferred embodiment, the phase-correction unit 192 retrieves the previously stored sign values of $\overline{U}_{AB}(n)$ or $\tilde{U}_{AB}(n)$ (see FIG. 6), and applies the signs to the respective input samples $P_{AB}(n)$ to generate output samples $S_{AB}(n)$. The output samples $S_{BC}(n)$ and $S_{CA}(n)$ may be similarly obtained. According to another embodiment, the phase-corrected conditional product signals ($S_{AB}$, $S_{BC}$, and $S_{CA}$) may be obtained by applying previously stored sign values to the square root of the respective conditional product signals $P_{AB}$, $P_{BC}$, and $P_{CA}$ so that the output signals have the voltage unit. According to yet another embodiment (not shown in the FIG. 7), the phase-corrected conditional product signal sample $S_{AB}(n)$ is obtained by averaging the first estimate $\tilde{U}_{AB}(n)$ and the second estimate $\overline{U}_{AB}(n)$ but with the exception that $S_{AB}(n)$ is set to zero if $\tilde{U}_{AB}(n)$ and $\overline{U}_{AB}(n)$ have opposite signs.

With reference to FIG. 7, as described above, by amplifying the signal component while suppressing the noise component, the conditional product signals $P_{AB}$, $P_{BC}$, and $P_{CA}$ have much higher signal-to-noise ratio (SNR) than their counterparts $U_{AB}$, $U_{BC}$, and $U_{CA}$. According to a preferred embodiment, a beat detection method 194 is used to analyze three conditional product signals $P_{AB}$, $P_{BC}$, and $P_{CA}$. One exemplary beat detection method 194 is an auto-sensing method, disclosed in U.S. Pat. No. 5,891,048, assigned to the assignee of the present patent application. In brief, the auto-sensing method applies a detection hold-off period after each peak detection, and then automatically adjusts the sensing threshold, which is adaptive to the measured peak amplitude of the QRS complex and varies in accordance with a predetermined time dependence. Therefore, for each conditional product signal, the beat detection method 194 generates a series of sense markers 196 for that specific channel. According to a preferred embodiment, the resulting three series of sense markers 196 are provided to a vote unit 198 for generating the final sense marker output signal 200. Specifically, if a QRS complex is detected in two out of three conditional product signals within a predefined time window (i.e. tolerance of difference in detection time), e.g. 50 ms, then a sense marker is generated for the final beat detection output. Otherwise (e.g., only one of the three conditional product signals has a beat detection), then no sense marker is generated for the final beat detection output. According to another embodiment of the invention, only if a QRS complex is detected in all three conditional product signals within a predefined time window (i.e. tolerance of difference in detection time), e.g., 50 ms, then a sense marker is generated for the final beat detection output. Yet, according to a further embodiment, if a QRS complex is detected in any one of the three conditional product signals, then a sense marker is generated for the final beat detection output. Other more advanced methods to generate the final beat detection output in response to three channels of sense markers may also be implemented, for example, by assigning different voting weights to the sense marker channels in response to an assessment of the signal to noise ratio of $P_{AB}$, $P_{BC}$, and $P_{CA}$, in which the signal power may be estimated from the conditional product amplitude at or around the sense marker (i.e. within the QRS complex), and the noise power may be estimated from the conditional product amplitude at or around the middle region between adjacent sense markers (i.e. within the T-P segment).

Figure 8:
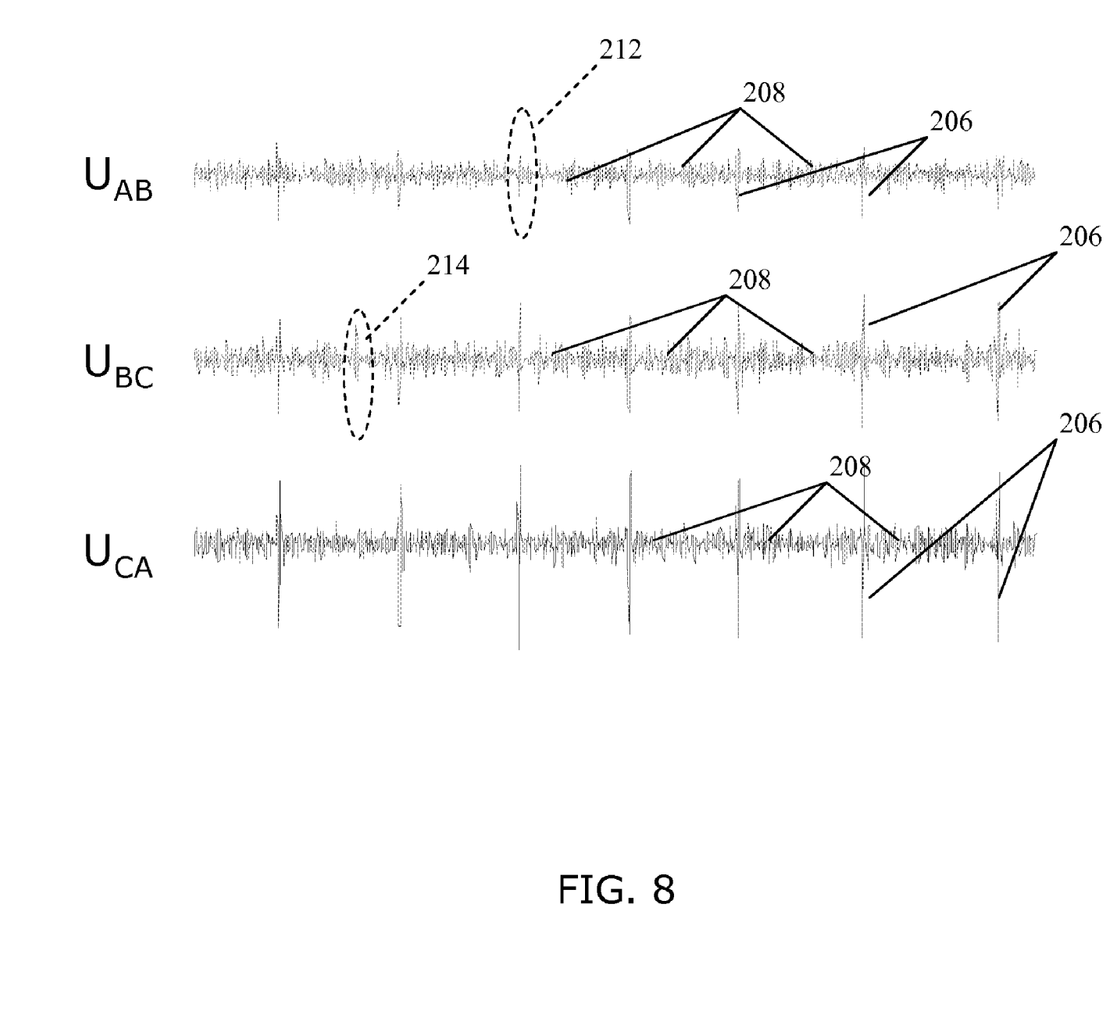
FIG. 8 shows an example of three time-multiplexed digital subcutaneous ECG signals $U_{AB}$, $U_{BC}$ and $U_{CA}$.

FIG. 8 shows an example of three channels of time-multiplexed digital subcutaneous ECG signals $U_{AB}$, $U_{BC}$ and $U_{CA}$. Despite filtering by the front-end circuit, the signals 206 are contaminated by high frequency noise 208. The noise power is only slightly lower than the signal power, such that it is difficult to differentiate some of the true QRS complex features, e.g. 212, from noise deflections, e.g. 214.

Figure 9:
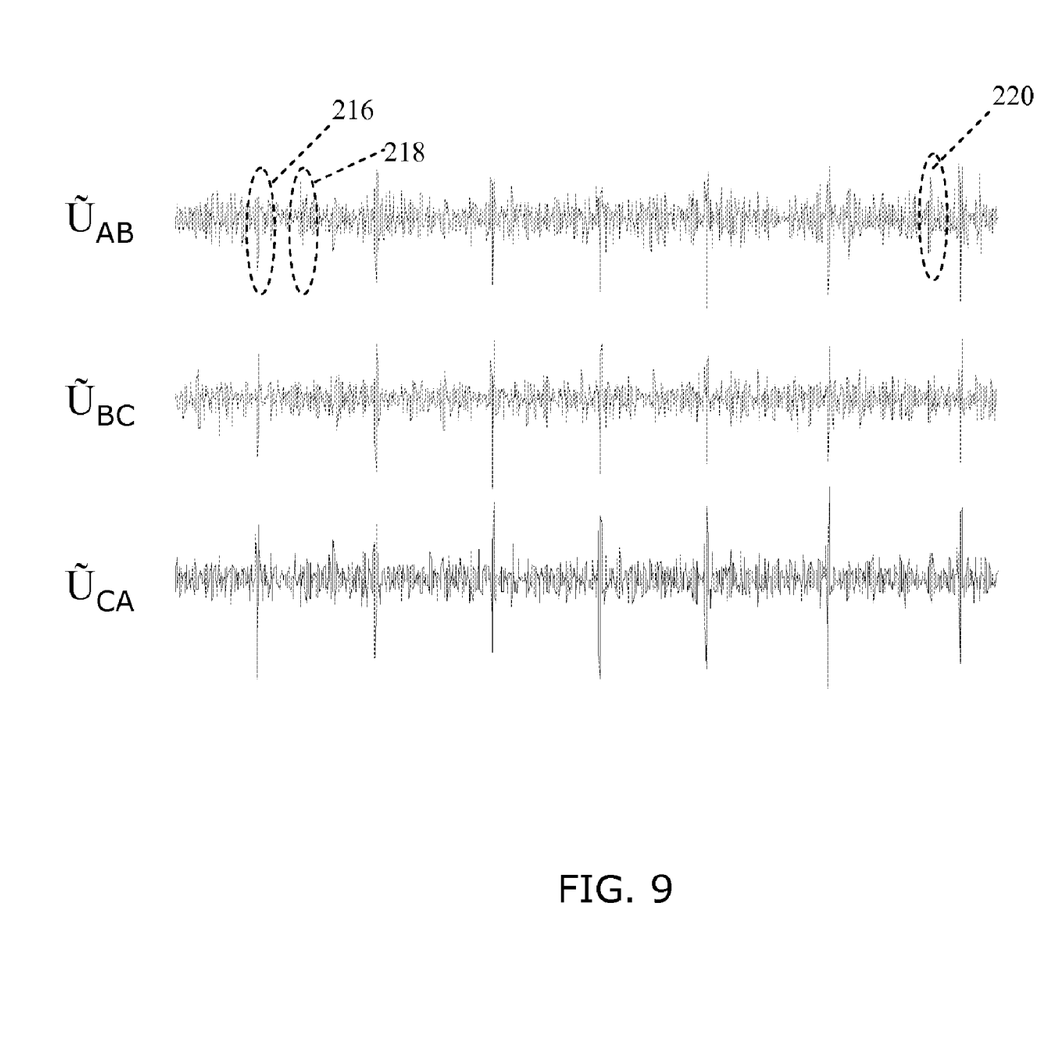
FIG. 9 shows three composite signals $\tilde{U}_{AB}$, $\tilde{U}_{BC}$, $\tilde{U}_{CA}$ that are estimated from the time-multiplexed differential signals $U_{AB}$, $U_{BC}$ and $U_{CA}$ shown in FIG. 8.

FIG. 9 shows the composite signals $\tilde{U}_{AB}$, $\tilde{U}_{BC}$, and $\tilde{U}_{CA}$ that are estimated from the time-multiplexed differential signals $U_{AB}$, $U_{BC}$ and $U_{CA}$. Although in general the estimated signals $\tilde{U}_{AB}$, $\tilde{U}_{BC}$, and $\tilde{U}_{CA}$ bear some similarity to the respective signals $U_{AB}$, $U_{BC}$ and $U_{CA}$, their morphological differences are also evident. Still, the estimated signals are contaminated by high frequency noise. The noise power is only slightly lower than the signal power, causing difficulty in differentiating some true QRS complexes, e.g., 216 from noise deflections, e.g., 218 and 220.

Figure 10:
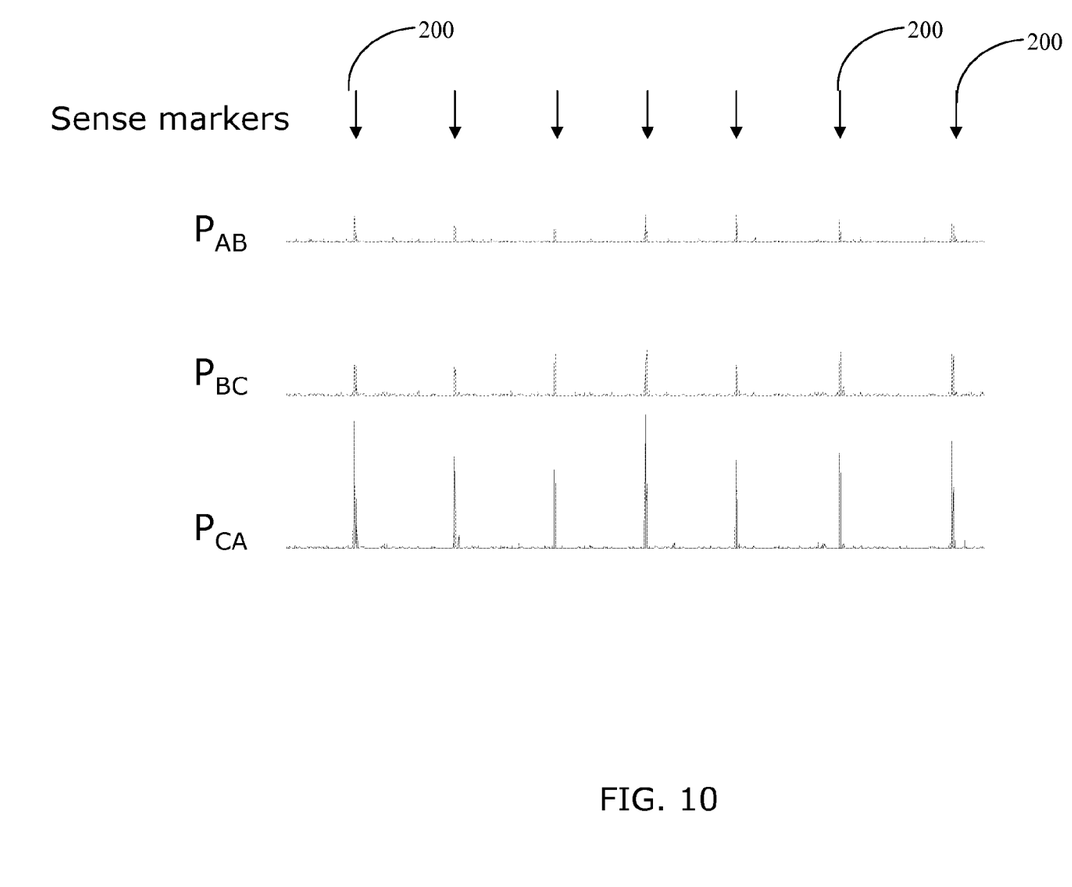
FIG. 10 shows three conditional product signals $P_{AB}$, $P_{BC}$, and $P_{CA}$ constructed from the first estimated signals $\tilde{U}_{AB}$, $\tilde{U}_{BC}$, $\tilde{U}_{CA}$, shown in FIG. 9, and second estimated signals $\overline{U}_{AB}$, $\overline{U}_{BC}$ and $\overline{U}_{CA}$, respectively.

FIG. 10 shows the conditional product signals $P_{AB}$, $P_{BC}$, and $P_{CA}$ that are respectively constructed from the first estimated signals $\tilde{U}_{AB}$, $\tilde{U}_{BC}$, $\tilde{U}_{CA}$, and the second estimated signals $\overline{U}_{AB}$, $\overline{U}_{BC}$ and $\overline{U}_{CA}$. In addition, the final sense markers 200 as determined by the method described above are also shown. Clearly, for each channel, the signal components (QRS complexes) are significantly enhanced whereas the noise components are substantially reduced. The spurious deflections observed in FIG. 7 and FIG. 8 are either confirmed or rejected as QRS complexes.

Figure 11:
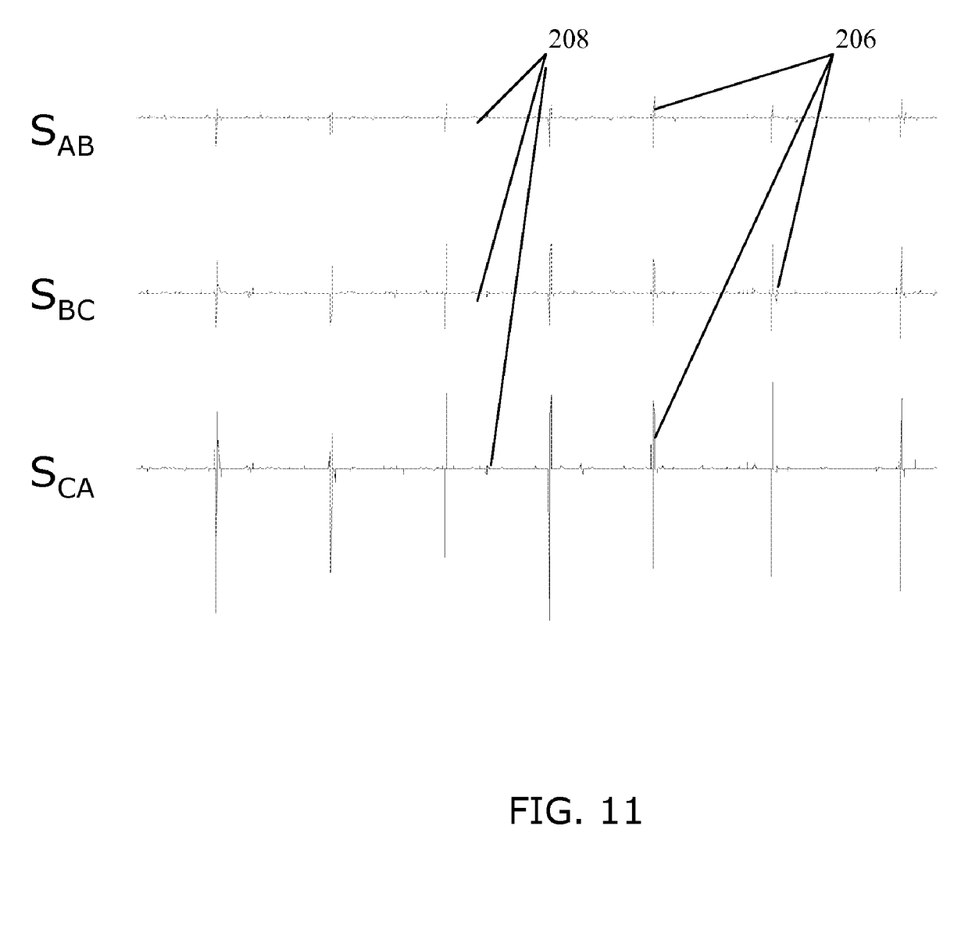
FIG. 11 shows phase-corrected conditional product signals $S_{AB}$, $S_{BC}$, and $S_{CA}$.

Finally, FIG. 11 shows phase-corrected conditional product signals $S_{AB}$, $S_{BC}$, and $S_{CA}$, which represent the final result of applying the disclosed method and apparatus. Compared to the original subcutaneous ECG signals $U_{AB}$, $U_{BC}$, and $U_{CA}$ shown in FIG. 8, a dramatic increase in SNR (i.e., a dramatic increase in the strength of QRS complex signals 206 and a dramatic decrease in the level of noise 208) is achieved for $S_{AB}$, $S_{BC}$, and $S_{CA}$. Furthermore, compared to the conditional product signals $P_{AB}$, $P_{BC}$, and $P_{CA}$, the phase-corrected signals $S_{AB}$, $S_{BC}$, and $S_{CA}$ also preserve phase information of the QRS complexes, thus making them more suitable for ECG interpretation and morphological analysis.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A method of enhancing the signal-to-noise ratio (SNR) of measured electrocardiogram (ECG) signals, the method comprising:
    providing at least three cardiac input signals derived from the measured ECG signals;
    forming a first estimate from each of at least three pairs of input signals;
    forming a second estimate from each of the input signals; and
    obtaining conditional product (CP) signals by generating, from each first estimate and each second estimate, a conditional product wherein the obtained CP signals exhibit increased signal components and reduced noise components, thus producing an enhanced ratio of signal to noise components (SNR).

2. The method of claim 1, wherein the first estimate is a differential signal and the second estimate is an averaged signal formed by using a weighted moving average filter.

3. The method of claim 1, wherein the measured ECG signals are of a type obtained from surface measurements.

4. The method of claim 1, wherein the measured ECG signals are of a type obtained from subcutaneous measurements.

5. The method of claim 1, wherein the enhanced SNR facilitates cardiac beat detection when the obtained conditional product signals are subject to peak detection using an auto-sensing approach.

6. The method of claim 2, wherein the conditional product depends on the relative polarities of the differential and averaged signals, such that if the differential and averaged signals have the same polarity, then the conditional product is obtained by calculating a sample-by sample-product of the differential signal and the average signal.

7. The method of claim 2, wherein the conditional product depends on the relative polarities of the differential and averaged signals, such that if the differential and averaged signals have different polarity, then the conditional product is set to zero.

8. A cardiac device for use in detecting heartbeats, to which at least three external sensing electrodes are attached to provide at least three analog voltage input signals, the device comprising an electrocardiogram (ECG) sensing unit for use in producing digital signals from the analog voltage input signals, wherein the sensing unit includes:
    a. a multiplexer;
    b. signal processing units; and
    c. a controller configured to enhance the signal to noise ratio (SNR) of the digital signals by generating conditional product signals from differential signals and weighted average signals, thereby facilitating heartbeat detection.

9. The cardiac device of claim 8, wherein if the differential signals and average signals have the same polarity, then the conditional product is obtained by calculating a sample-by sample-product of the differential signal and the average signal.

10. The cardiac device of claim 8, wherein if the differential signals and average signals have different polarity, then the conditional product is set to zero.

11. The cardiac device of claim 8, wherein the signal processing units are selected from the group consisting of differential amplifiers, analog filters, analog-to-digital converters, and digital filters.

12. The cardiac device of claim 8, further comprising on-board biological input sensors.

13. The cardiac device of claim 8, further comprising an impedance sensor for use in monitoring integrity of the sensing electrodes.

14. The cardiac device of claim 8, being implantable in the chest of a human or animal subject, the device further comprising:
    an RF unit for use in communicating signals to external parties; and
    a biocompatible housing containing the RF unit, the ECG sensing unit, and the controller.

15. In an implantable cardiac device, to which at least three external sensing electrodes are attached to provide at least three analog ECG voltage input signals for subcutaneous monitoring of cardiac electrical activity, the improvement comprising:
    a plurality of signal processing units for producing digital ECG signals from the analog ECG voltage input signals; and
    a processor programmed to construct, from first and second estimates of the digital ECG signals, at least three conditional product signals that exhibit enhanced signal-to-noise ratios for ease in detecting heart beats.

16. The cardiac device of claim 15, wherein
    the first estimate is a differential signal,
    the second estimate is a weighted average signal, and,
    if the differential and average signals have the same polarity, then the conditional product signals are generated by multiplying, point-by-point, sample pairs of differential signals and averaged signals.

17. The cardiac device of claim 15, wherein the first estimate is a differential signal, the second estimate is a weighted average signal, and, if the differential and average signals have the same polarity, the conditional product signals are set to zero.

18. The cardiac device of claim 15, wherein the signal processing units are selected from the group consisting of differential amplifiers, analog filters, analog-to-digital converters, and digital filters.

19. The method of claim 1, wherein the first estimate is a differential signal representing the difference between input signals.

20. The method of claim 1, wherein the second estimate is an averaged signal representing the average of input signals.

* * * * *